United States Patent [19]
Coates

[11] Patent Number: 5,997,470
[45] Date of Patent: Dec. 7, 1999

[54] PENILE TUBE AND CONSTRICTOR RING REMOVAL GUIDE SYSTEM AND METHOD OF USE

[76] Inventor: Frank Coates, G122 Main Street Apartments, 1158 W. Main St., Lansdale, Pa. 19446

[21] Appl. No.: 08/993,897

[22] Filed: Dec. 18, 1997

Related U.S. Application Data

[60] Provisional application No. 60/033,944, Dec. 23, 1996, and provisional application No. 60/042,285, Apr. 1, 1997.

[51] Int. Cl.⁶ .................................................... A61F 5/00
[52] U.S. Cl. .............................................................. 600/41
[58] Field of Search .......................................... 600/35–41

[56] References Cited

U.S. PATENT DOCUMENTS

| | | |
|---|---|---|
| D. 293,473 | 12/1987 | Chaney . |
| 2,874,698 | 2/1959 | Sell .......................................... 600/38 |
| 4,539,980 | 9/1985 | Chaney . |
| 4,628,915 | 12/1986 | Chaney . |
| 4,741,329 | 5/1988 | Marcune . |
| 4,753,227 | 6/1988 | Yanuck, Jr. ............................... 600/41 |
| 5,195,943 | 3/1993 | Chaney .................................... 600/38 |
| 5,462,514 | 10/1995 | Harris ....................................... 600/38 |
| 5,624,378 | 4/1997 | Baldecchi ................................. 600/38 |

OTHER PUBLICATIONS

Encore User's Manual, VTU–1™ System, Encore, Inc. (Rev. May 1994).

*Primary Examiner*—Samuel Gilbert
*Attorney, Agent, or Firm*—Ratner & Prestia

[57] ABSTRACT

An improved penile tube and removal guide for use in a vacuum therapy system for achieving and maintaining an erection. The penile tube has an open, tapered end into which the penis is inserted and a stop ring positioned along the penile tube toward the tapered end. The removal guide has a stepped inner surface having a larger diameter portion and a smaller diameter portion which are concentrically located along the axis of the removal guide. The removal guide is mounted circumferentially on the penile tube and freely slides along the longitudinal axis of penile tube away from the tapered end of the penile tube until an inner flange of the smaller diameter portion engages the stop ring. The penile tube, stop ring, and stepped removal guide facilitate the placement of a configuration ring upon a penis while maintaining a vacuum in the penile tube. A mounting cone having a conical portion facilitates sliding the constriction ring onto the transfer sleeve of the penile tube. The mounting cone has a cylindrical end located opposite the conical portion and having an inner surface which contains a recess configured to fit over tapered end of penile tube.

15 Claims, 20 Drawing Sheets

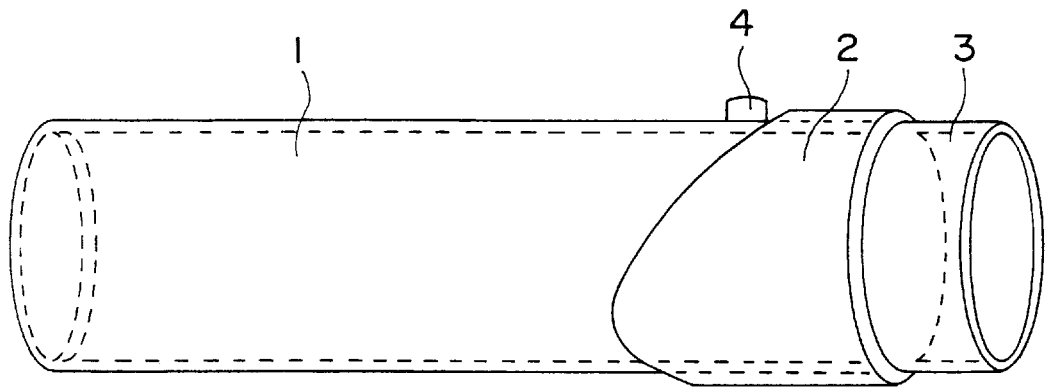
FIG. 1
PRIOR ART
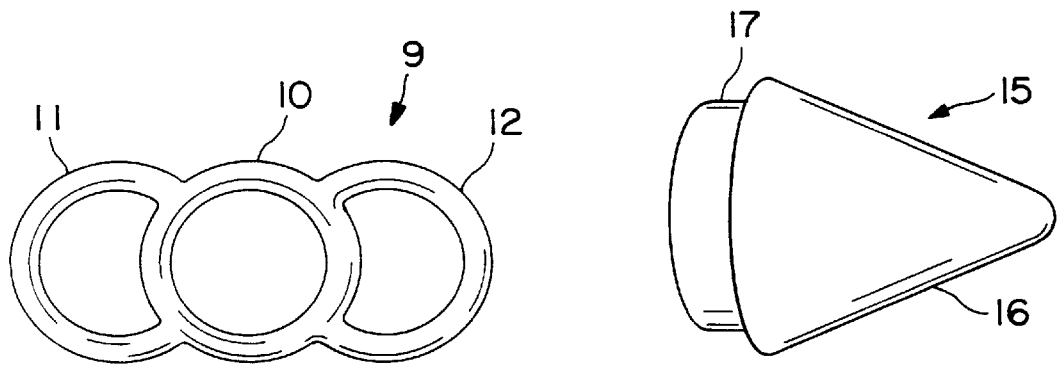
FIG. 2
PRIOR ART
FIG. 3
PRIOR ART
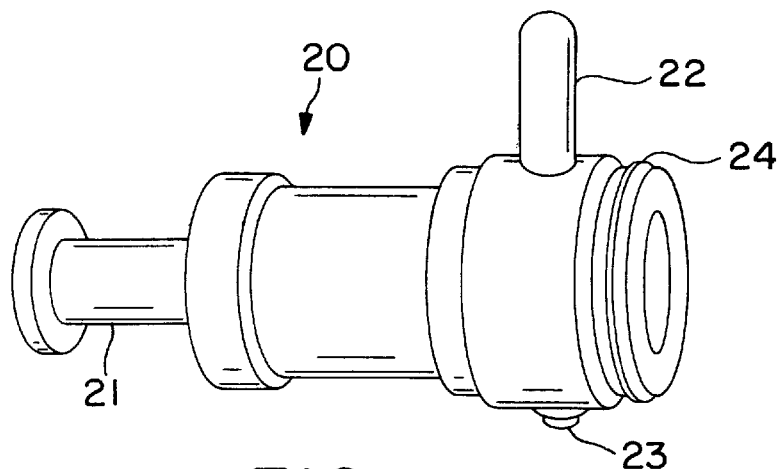
FIG. 4
PRIOR ART

PENILE TUBE AND CONSTRICTOR RING REMOVAL GUIDE SYSTEM AND METHOD OF USE

This application claims benefit of provisional application number 60/033,944 filed Dec. 23, 1996. This application claims benefit of provisional application number 60/042,285 filed Apr. 1, 1997.

FIELD OF THE INVENTION

This invention relates to a device for assisting a male to obtain and maintain an erection of his penis to enable performing sexual intercourse.

BACKGROUND OF THE INVENTION

Medical literature reveals that males at all ages sometimes inexplicably lose the capability of obtaining an erection for a variety of reasons and even without apparent reasons. In some cases there are psychological causes and in other cases physiological causes underlying the inability to obtain or maintain an erection. Regardless of the cause of impotency, however, in most cases the male maintains the desire and urge to indulge in intercourse.

Development of a penile erection is, of course, dependent on a complex interaction of psychological and physiological factors which are not clearly understood, however, the anatomical phenomena associated with successful erection are well known. The penis is composed of recital tissue arranged in three longitudinal columns bonded by fibrous tissue. Erectile tissue has a sponge-like structure containing cavernous spaces for being occupied by blood. These spaces are fed by arterioles and capillaries and are drained by small flow restricting veins. Muscle fibers traverse the walls of the spaces and surround their discharge veins. When the penis is induced to erect, arterioles feeding the spaces dilate, the muscle fibers around the spaces relax, and the muscle controlling the venous outlets contract to restrict blood discharge from the caverns. The cavernous spaces in the erectile tissue expand as blood is pumped through them at high pressure and the penis becomes hard and erect. Thus, the natural erection process is basically a matter of capturing and holding pressurized blood in the cavernous tissues of the penis.

Surgically implantable devices have been developed for enabling a male subject to simulate a natural penile erection. Typically, one or more longitudinally extending expandable sacs are implanted in the penis and connected through a fluid system having check valves to a fluid filled bulb that can be massaged externally for pumping the fluid into the sac to thereby simulate the natural process. Some implants cause permanent erections. Implantation of some of the artificial devices result in permanent destruction of the nerve and blood vessel passages such that a natural erection can never again be obtained. All the implant techniques require the subject to spend some time in a hospital. The hospital and surgical expense is known to be substantial.

In the prior art there are devices which can be applied externally of the penis for maintaining an erection. The device is called a pubis ring. It is intended for use primarily by those males who, when excited, can develop an erection but cannot maintain it for a long enough time to satisfy themselves and their mate during intercourse. The pubis ring is designed to keep the blood in the penis once it has been pressurized by natural reaction to sexual stimuli. It cannot help in cases where there is a minimal erection or none at all. The pubis ring comprises a loop whose opposite ends enter the opposite ends of a flexible sleeve. The two ends emerge together out of a radial hole in the sleeve. The loop is slipped back to the root of the penis at a time when the subject perceives as a result of prior experience that his erection is likely to be at its maximum even though he may remember that there were times in the past when it could become larger and more rigid. When a maximum erection is perceived, the cords of the loop are snubbed to trap the pressurized blood in the penis. The erection can then be maintained for its intended purpose. Disadvantages of the pubic ring are that it requires some dexterity to secure and focusing attention on the securing problem can be distracting enough to cause the tentative erection to disappear prior to usage.

Other elastic rings for maintaining an erection are disclosed in U.S. Pat. Nos. 4,539,980 and 4,628,915, issued to Chaney. Briefly stated, the basic form of the erection assisting device disclosed in these patents comprises a constriction ring having an elastic ring centered between two elastic loops which are attached to the periphery of the ring on its opposite sides or at the first and third quadrants of the ring. The loops are used to stretch the ring radially outwardly to enlarge its opening sufficiently for it to fit over the root of the penis where it is released and contracts to pinch off the blood vessels leading to and from the penis. The user must then massage blood forwardly into the penis by strokes applied with the hand and fingers beginning substantially rearwardly of the scrotum to thereby develop local blood pressure sufficient to overcome the sealing force of the ring and pressurize the caverns in the penis which results in an erection. Use of the elastic rings disclosed by Chaney requires dexterity on the part of the user to stretch the central ring quadrilaterally so it clears the outside of the penis as it is being applied. Thus, to facilitate the positioning of the elastic rings on the penis, Chaney also discloses a cone and cylindrical carrier sleeve mounting apparatus.

The patents to Chaney report that the elastic constriction ring and mounting devices not only help a male to maintain but also facilitate manually achieving an erection after the device has been deposited on the penis. This is accomplished by the male user pressing his hand in the groin or crotch area and massaging blood forwardly into the penis against the elastic pressure created by the elastic ring. When a massage stroke is terminated, the elastic ring acts to prevent outflow. After several massage strokes, enough blood will be manually forced into the penis and enough pressure will be developed to produce a lasting erection.

In an attempt to further automate the erection process, a vacuum therapy system has also been described which enhances the ability of a user to achieve an erection by applying a vacuum to the penis prior to placement of the constriction ring. Such a system is available as the VTU-1™ System available from Encore, Inc. Louisville, Ky. and is shown in FIGS. 1–8. FIGS. 14 show the separable components of a conventional vacuum therapy system for assisting in the attainment and maintenance of an erection. FIG. 1 shows a penile tube 1 which is typically a transparent plastic tube and has a guide post 4. A removal guide 2 is mounted circumferentially on the penile tube 1 and located to define a transfer sleeve 3 portion at one end of the penile tube 1. Shown in FIG. 2 is a constriction ring 9 having an elastic, preferably latex, center ring 10 which has a circular cross-section and has two finger-gripping loops 11 and 12 molded integrally with the central ring. FIG. 3 shows a mounting cone 15 which has conical portion 16 to facilitate sliding constriction ring 9 onto the transfer sleeve 3 of penile tube 1. Mounting cone 15 has a cylindrical end 17 located opposite conical portion 16. A vacuum pump 20 is shown in FIG. 4 and has handle 21, thumb grip 22, release valve 23, and seal 24.

FIG. 5 shows the components of FIGS. 1–4 after assembly which is accomplished by inserting the cylindrical end 17 of mounting cone 15 into the end of penile tube 1 having the transfer sleeve 3 and inserting the seal 24 of the vacuum pump 20 into the opposite end of the penile tube 1. FIG. 6 shows a constriction ring 9 in the process of being mounted onto transfer sleeve 3 of penile tube 1. This is accomplished by holding and pulling on loops 11 and 12 of constriction ring 9 to enlarge center ring 10 so that the constriction ring 9 may be slid over the conical portion 16 of mounting cone 15 and onto transfer sleeve 3. Upon removal of the mounting cone 15, the constriction ring 9 is mounted and ready for insertion upon a penis as shown in FIGS. 7 and 8.

Shown in FIG. 7 is a user having a flaccid penis inserted into the penile tube 1. A constriction ring 9 is mounted on transfer sleeve 3, as described above with respect to FIG. 6. The end of the penile tube 1 which contacts the body at the base of the penis is typically lubricated before inserting the penis in order to assist in sealing penile tube 1 against the user's body so that a vacuum may be drawn. By applying slight pressure to the penile tube 1 toward the body of the user and pumping handle 21 of vacuum pump 20, as shown, a vacuum is drawn in penile tube 1 to cause the penis to become engorged with blood, thus achieving an erection. The thumb grip 22 may be used to steady the vacuum system during pumping handle 21.

As soon as the desired erection has been achieved, the constriction ring 9 is then placed at the base of the penis to maintain the state of engorgement with blood. As shown in FIG. 8, this is accomplished while holding penile tube 1 tightly against the body of the user by rotating removal guide 2 in the direction of arrow A to force removal guide 2 to ride against guide post 4 and move removal guide 2 toward the user in the direction of arrow B. The movement of removal guide 2 toward the user in this manner forces constriction ring 9 to move off of the transfer sleeve 3 in the direction of arrow B and onto the base of the penis. Upon placing the constriction ring 9 on the penis, center ring 10 contracts onto the base or root of the erect penis to prevent outflow of venous blood drawn by the vacuum created within the penile tube 1.

The final step to permit the user to engage in sexual intercourse, is the removal the vacuum system from the body of the user. Although during the transfer of the constriction ring much of the vacuum within the penile tube 1 is lost, any vacuum remaining must be released. This is accomplished by depressing release valve 23 of vacuum pump 20 to permit the vacuum pump 20 and penile tube 1 to be removed from the body of the user.

This conventional vacuum therapy system, which is described above with respect to FIGS. 1–8, is difficult to use and has attendant deficiencies with respect to achieving and maintaining a satisfactory vacuum while placing a constriction ring on the penis. As a result, the conventional vacuum system requires dexterity on the part of the user and even with such dexterity, the resultant erection may not be maximized given that a satisfactory vacuum may not be achieved or maintained. Furthermore, because the conventional vacuum system requires additional attention on the part of the user, focusing attention to the use of the vacuum system may be distracting enough to cause the benefit of any natural ability to obtain an erection on the part of the user to be lost.

The present invention overcomes the limitations, difficulties, and shortcomings of these prior art devices by providing a conditioning apparatus which can be easily used to achieve and maintain an erection by sequentially applying a vacuum and placing a constriction ring to a penis while limiting vacuum loss prior to placement of the constriction ring.

SUMMARY OF THE INVENTION

The present invention provides an improved penile tube and removal guide for use in a vacuum therapy system for achieving and maintaining an erection by sequentially applying a vacuum and placing a constriction ring to a penis. The penile tube has an open, tapered end into which the penis is inserted and a stop ring positioned along the penile tube toward the tapered end. The removal guide has a stepped inner surface having a larger diameter portion and a smaller diameter portion which are concentrically located along the axis of the removal guide. The removal guide is mounted circumferentially on the penile tube. A mounting cone is provided which has a conical portion to facilitate sliding the constriction ring onto the transfer sleeve of the penile tube. The mounting cone has a cylindrical end located opposite the conical portion and having an inner surface which contains a recess configured to fit over tapered end of penile tube.

Also provided is a vacuum assembly having a threaded penile tube with a ribbed transfer sleeve having a ribbed or fluted surface which facilitates movement of a constriction ring over the transfer sleeve onto a penis. A threaded penile tube and threaded removal guide assembly in conjunction with a spacer sleeve is also provided which facilitates the removal of constriction ring from the ribbed transfer sleeve. An additional mounting cone is provided which fits into the interior of ribbed transfer sleeve and has a cylindrical hole located along the longitudinal axis to facilitate insertion and removal of the mounting cone.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which:

FIG. 1 is planar view of a conventional penile tube;

FIG. 2 is a planar view of a conventional constriction ring;

FIG. 3 is a planar view of a conventional mounting cone;

FIG. 4 is a planar view of a conventional vacuum pump;

DETAILED DESCRIPTION OF THE INVENTION

Figure 5:
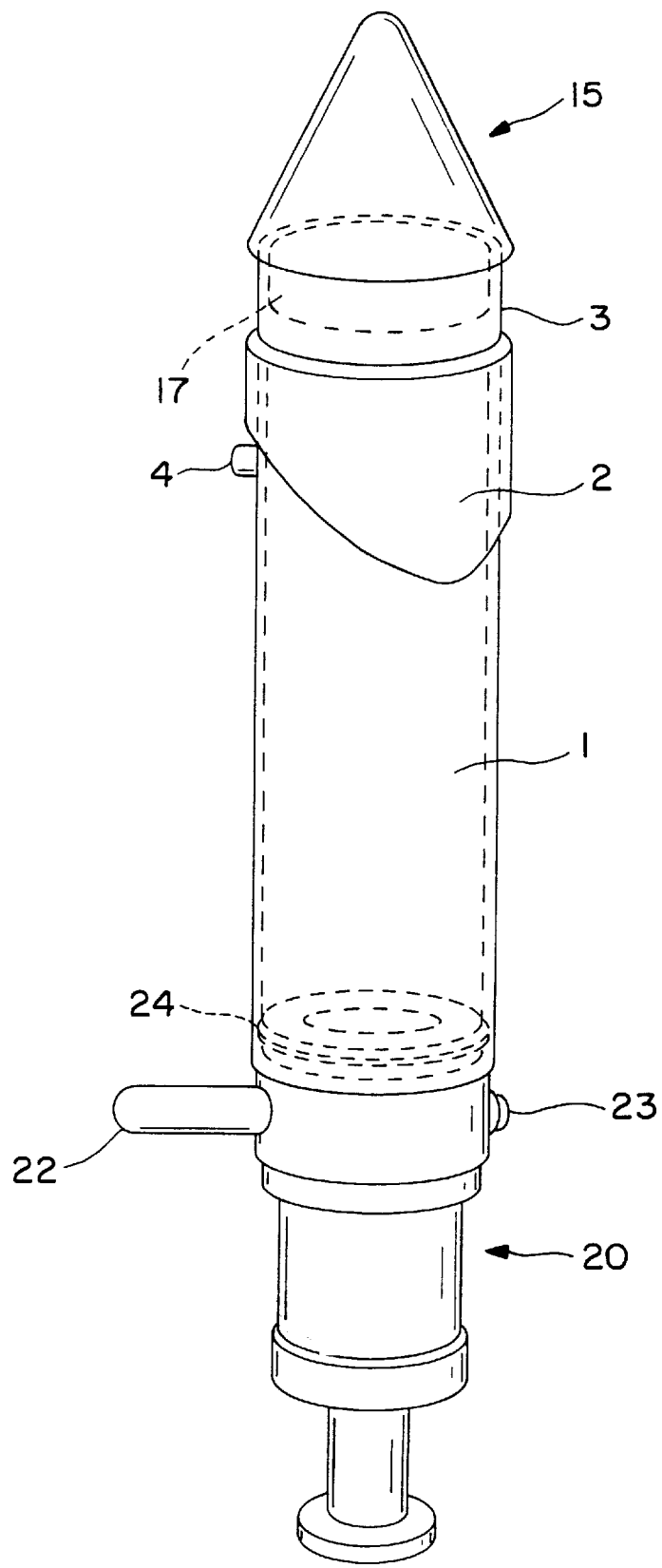
FIG. 5 is planar view of the conventional vacuum pump shown in FIG. 4 and the conventional mounting cone shown in FIG. 3 assembled to the ends of the penile tube shown in FIG. 1 of a conventional vacuum assembly.
Figure 6:
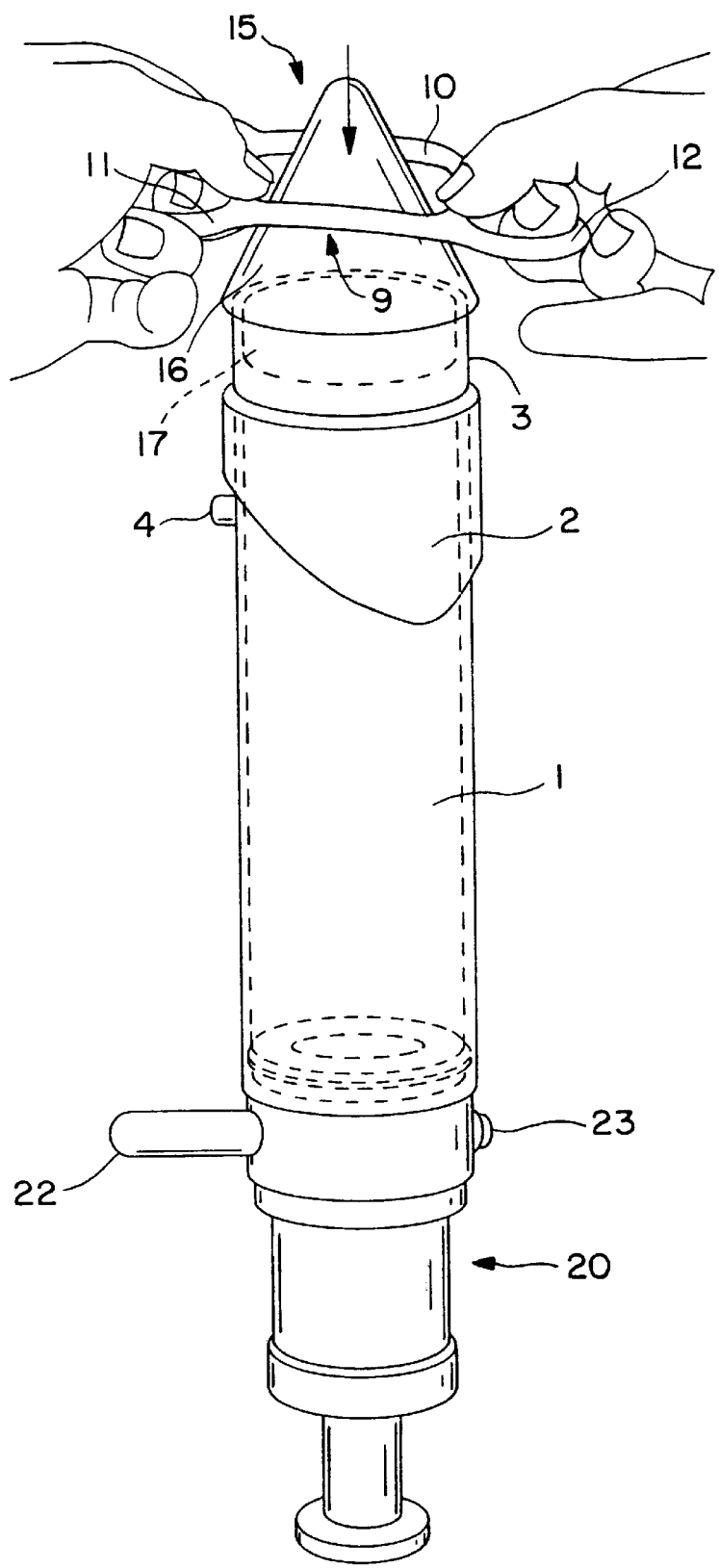
FIG. 6 is a planar view of the conventional vacuum assembly of FIG. 5 in the process of being mounted with a constriction ring.
Figure 7:
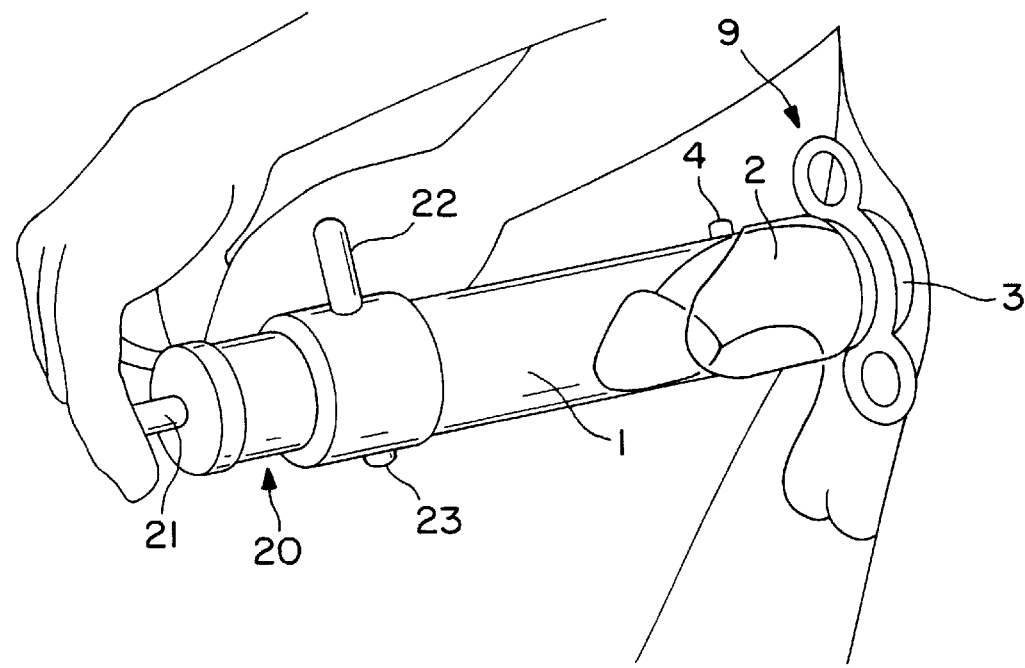
FIG. 7 is a planar view of the conventional vacuum assembly of FIG. 6 showing a penile tube after removal of the mounting cone and with a constriction ring in the process of being placed upon the base of a penis to be erected.
Figure 8:
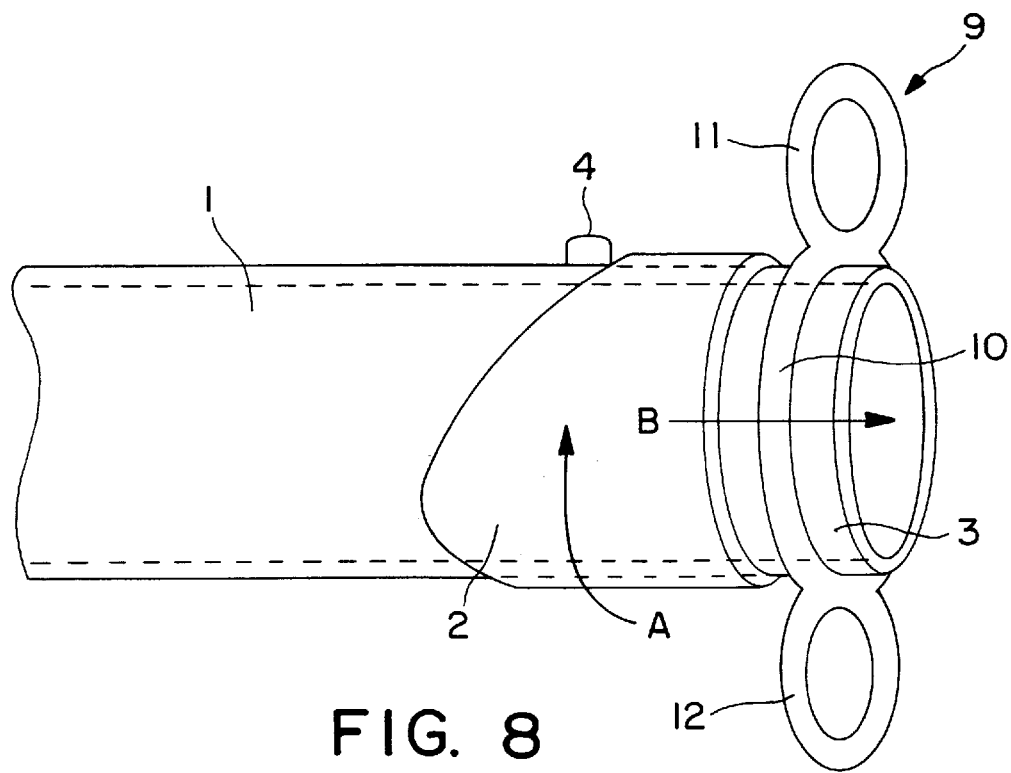
FIG. 8 is an enlarged planar view showing the penile tube and mounted constriction ring of FIG. 7.

It is emphasized that, according to common practice, the various dimensions of the conditioning apparatus of the present invention as shown in the drawings are not necessarily to scale. On the contrary, the width or length and thickness of the various dimensions may be arbitrarily expanded or reduced for clarity. The various dimensions of the components may be varied to accommodate design and manufacturing requirements as will be readily understood by those having ordinary skill in the art.

As discussed above, the conventional vacuum system described above is difficult to use and has attendant deficiencies with respect to achieving and maintaining a satisfactory vacuum while placing a constriction ring on the penis. In using the conventional vacuum apparatus shown in FIGS. 1–8, it is difficult to remove the constriction ring 9 from the transfer sleeve 3 to the base of the penis without losing a significant portion of the vacuum drawn within the penile tube 1. This is caused by the twisting motion required to rotate removal guide 2 around the longitudinal axis of penile tube 1 in order to effectively move constriction ring 9 off of transfer sleeve 3. The twisting motion applied to the removal guide 2, causes penile tube 1 to rock and move at the base of the penis such that the vacuum within the penile tube 1 is progressively lost. Moreover, operation of the conventional vacuum system typically requires two people to achieve placement of the constriction ring upon the penis.

Figure 9:
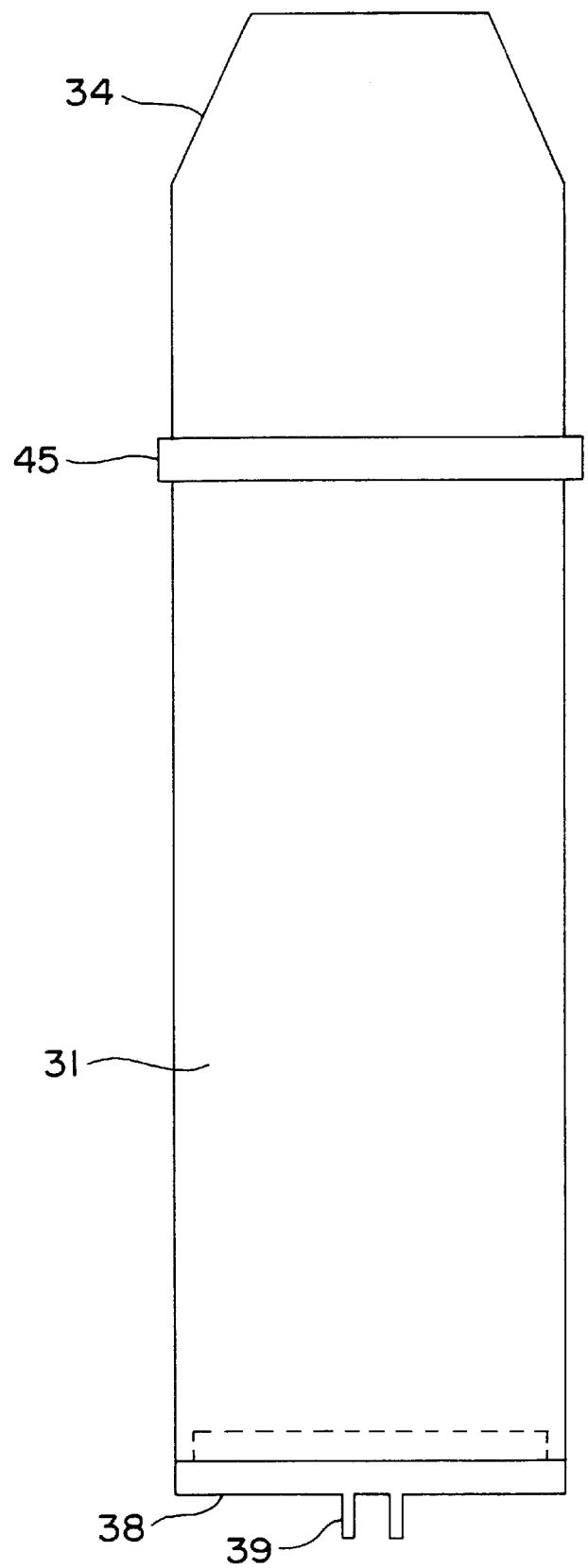
FIG. 9 is a planar view of a penile tube having a tapered end and a stop ring according to the present invention.
Figure 10:
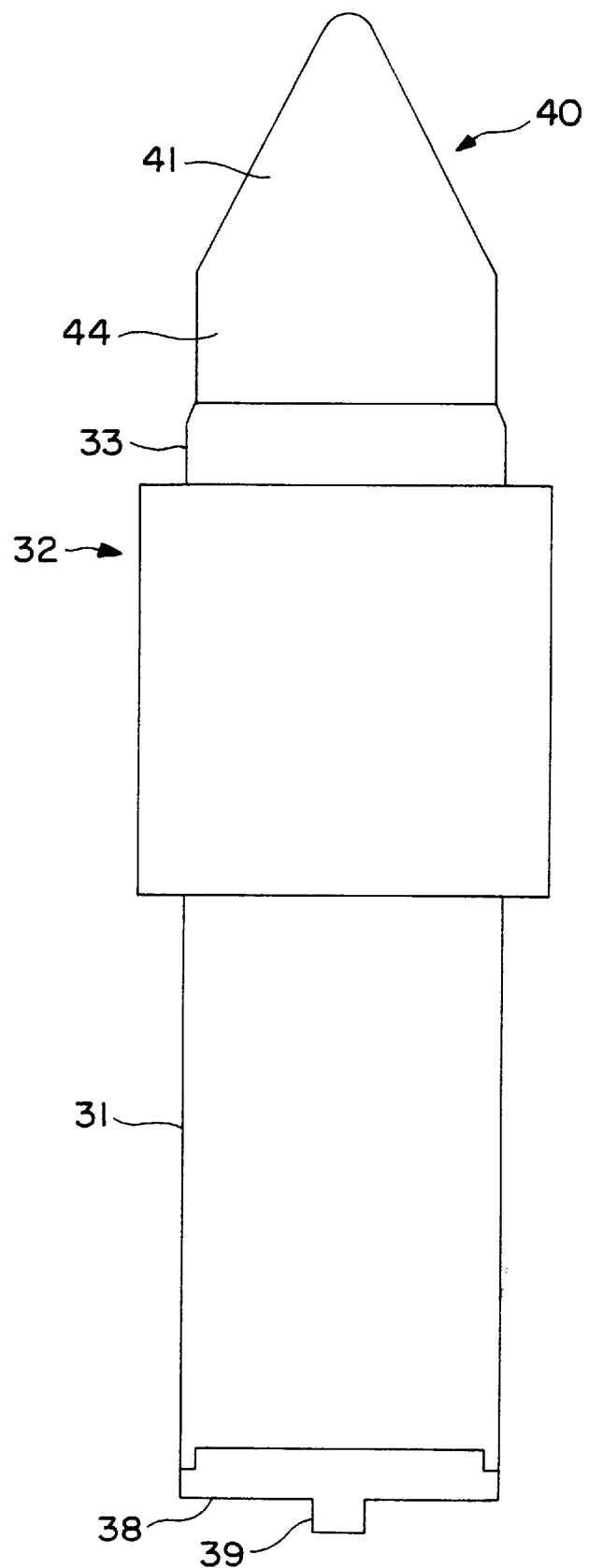
FIG. 10 is a planar view of the tapered penile tube of FIG. 9 with a stepped removal guide located concentrically on the penile tube and a mounting cone assembled to tapered end of the penile tube according to the present invention.
Figure 11:
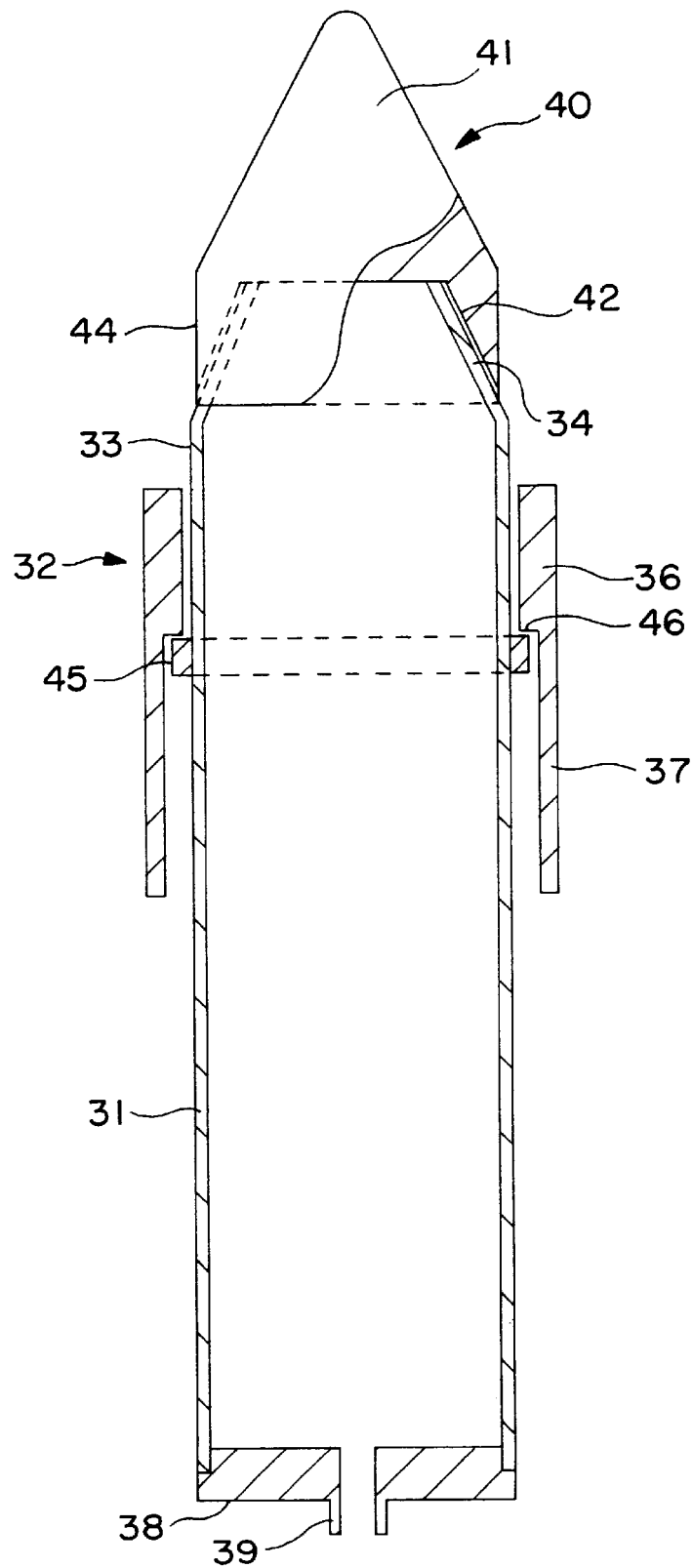
FIG. 11 is a partial cross-sectional view of the penile tube, stepped removal guide, and mounting cone of FIG. 10 taken along the longitudinal axis of the penile tube.
Figure 12:
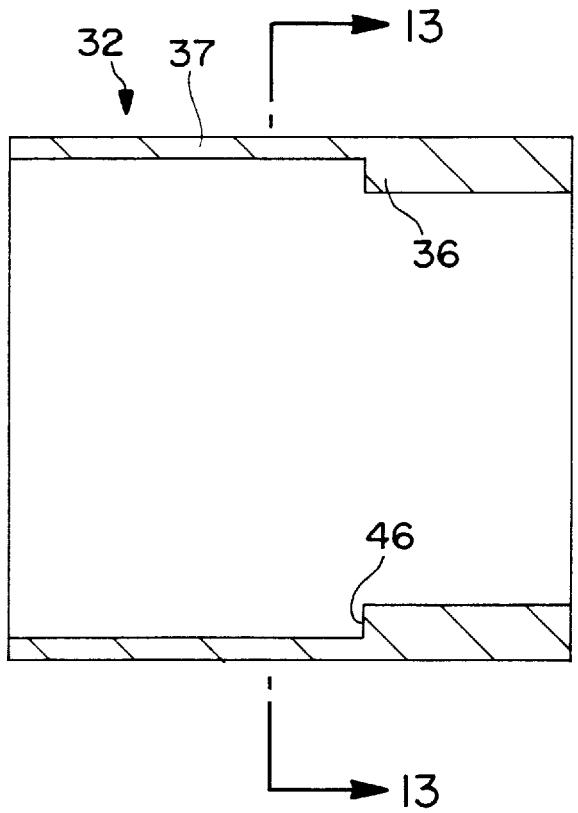
FIG. 12 is a cross-sectional view of the stepped removal guide of FIG. 11.
Figure 13:
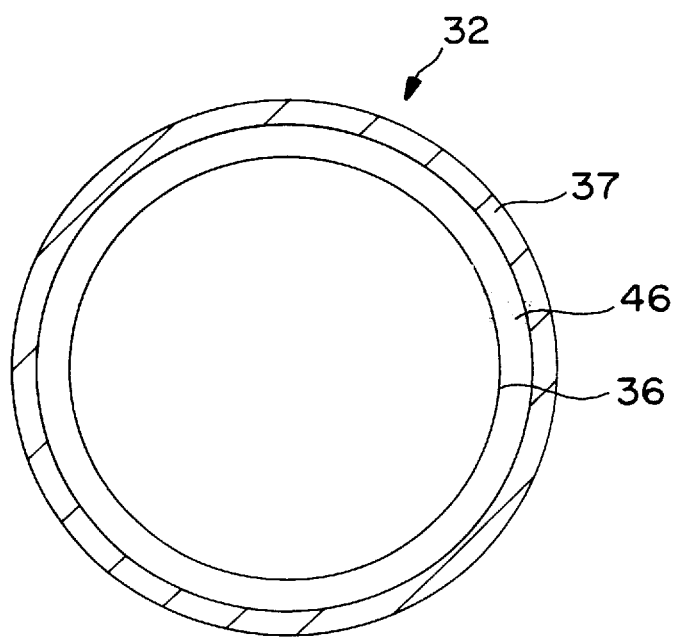
FIG. 13 is a cross-sectional view of the stepped removal guide of FIG. 12 taken along the sectional line 13—13.

The drawbacks of the conventional vacuum system are remedied by the present invention which is shown in FIGS. 9–29 and described below. Referring now to the drawing, wherein like reference numerals refer to like elements throughout, FIG. 9, shows an improved penile tube 31 for use in a vacuum therapy system according to one embodiment of the present invention as shown in FIGS. 9–18. The penile tube 31 has an open, tapered end 34 into which the penis is inserted. A stop ring 45 is positioned along the penile tube 31 toward the tapered end 34 as shown. A mounting cone 40 is shown inserted over the tapered end 34 as shown in FIGS. 10 and 11. As shown in the partial cross-sectional view in FIG. 11, mounting cone 40 has a cylindrical end 44 located opposite conical portion 41. Cylindrical end 44 has an outer surface with an outer diameter which is approximately equal to the outer diameter of penile tube 31. Cylindrical end 44 has an inner surface which contains a recess 42 configured to fit over tapered end 34 of penile tube 31. Preferably, recess 42 is contoured to provide a friction fit with tapered end 34.

Also shown in FIG. 10 is an improved removal guide 32 mounted circumferentially on the penile tube 31 according to the present invention. Removal guide 32 is shown in cross-sectional views in FIGS. 11–13 and has stepped inner surface having a larger diameter portion 37 and a smaller diameter portion 36 which are concentrically located along the axis of the removal guide 32. An inner flange 46 is defined by the smaller diameter portion 36 at the transition portion between the smaller diameter portion 36 and the larger diameter portion 37 of removal guide 32. A vacuum cap 38, shown in FIGS. 9–11, is inserted into the end opposite tapered end 34 of penile tube 31 and has nozzle 39 for facilitating the attachment of a vacuum source (not shown).

Figure 14:
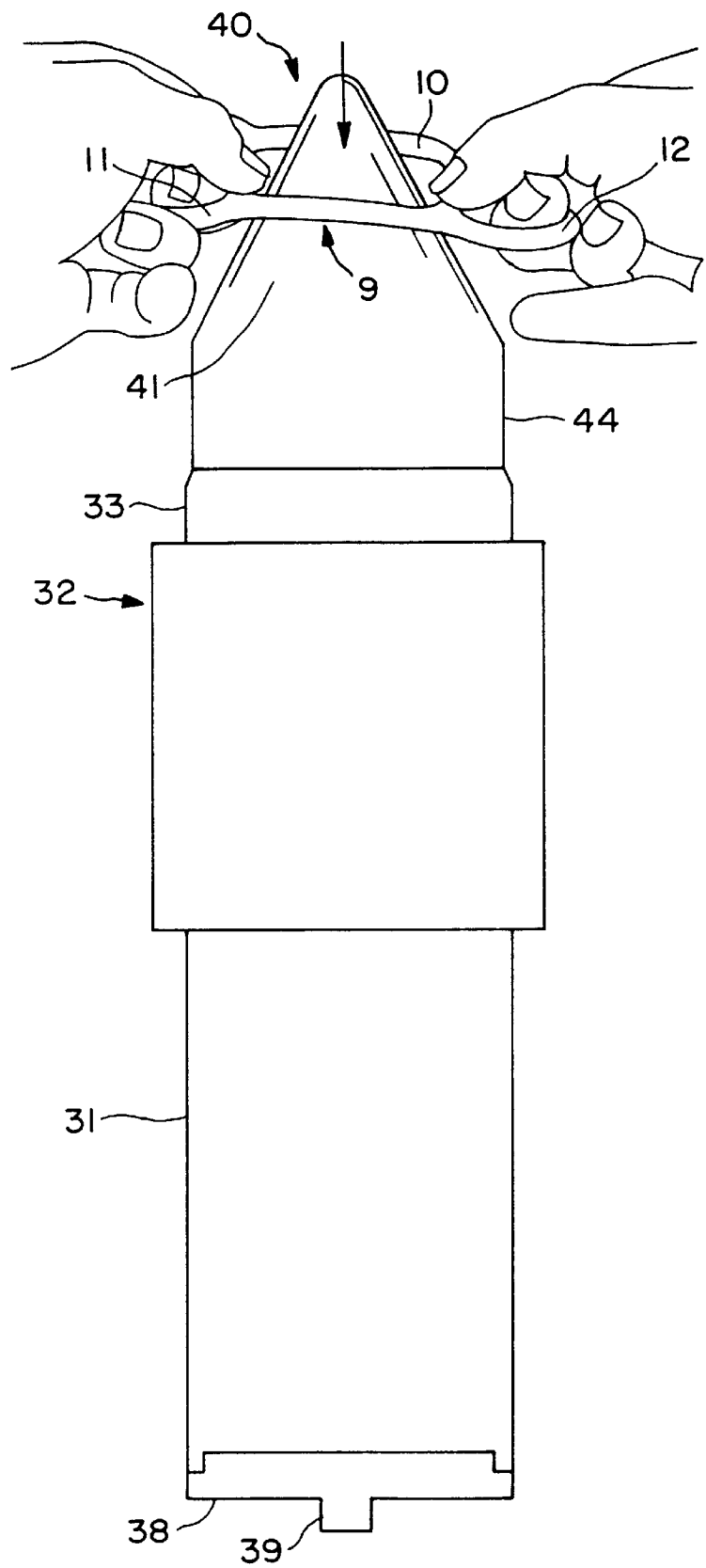
FIG. 14 is a planar view of the vacuum assembly of FIG. 11 according to the present invention in the process of being mounted with a constriction ring.

As shown in FIG. 11, the diameter of the smaller diameter portion 36 is slightly larger that the outer diameter of penile tube 31 while the diameter of the larger diameter portion 37 is slightly larger that the outer diameter of stop ring 45. Removal guide 32 freely slides along the longitudinal axis of penile tube 31 toward the vacuum cap 38 until the inner flange 46 engages stop ring 45. As shown in FIGS. 11 and 14, upon moving removal guide 32 toward vacuum cap 38 in this manner, a transfer sleeve portion 33 is defined which is the exposed cylindrical portion of penile tube 31 between the removal guide 32 and mounting cone 40. The length of transfer sleeve portion 33 may be varied by moving stop ring 45 along the longitudinal axis of penile tube 31 to define the range of motion of removal guide 32 along penile tube 31. Preferably, stop ring 45 is located in order to permit transfer sleeve portion 33 to move toward vacuum cap 38 and expose a transfer sleeve portion 33 of at least 0.5 inches.

Figure 15:
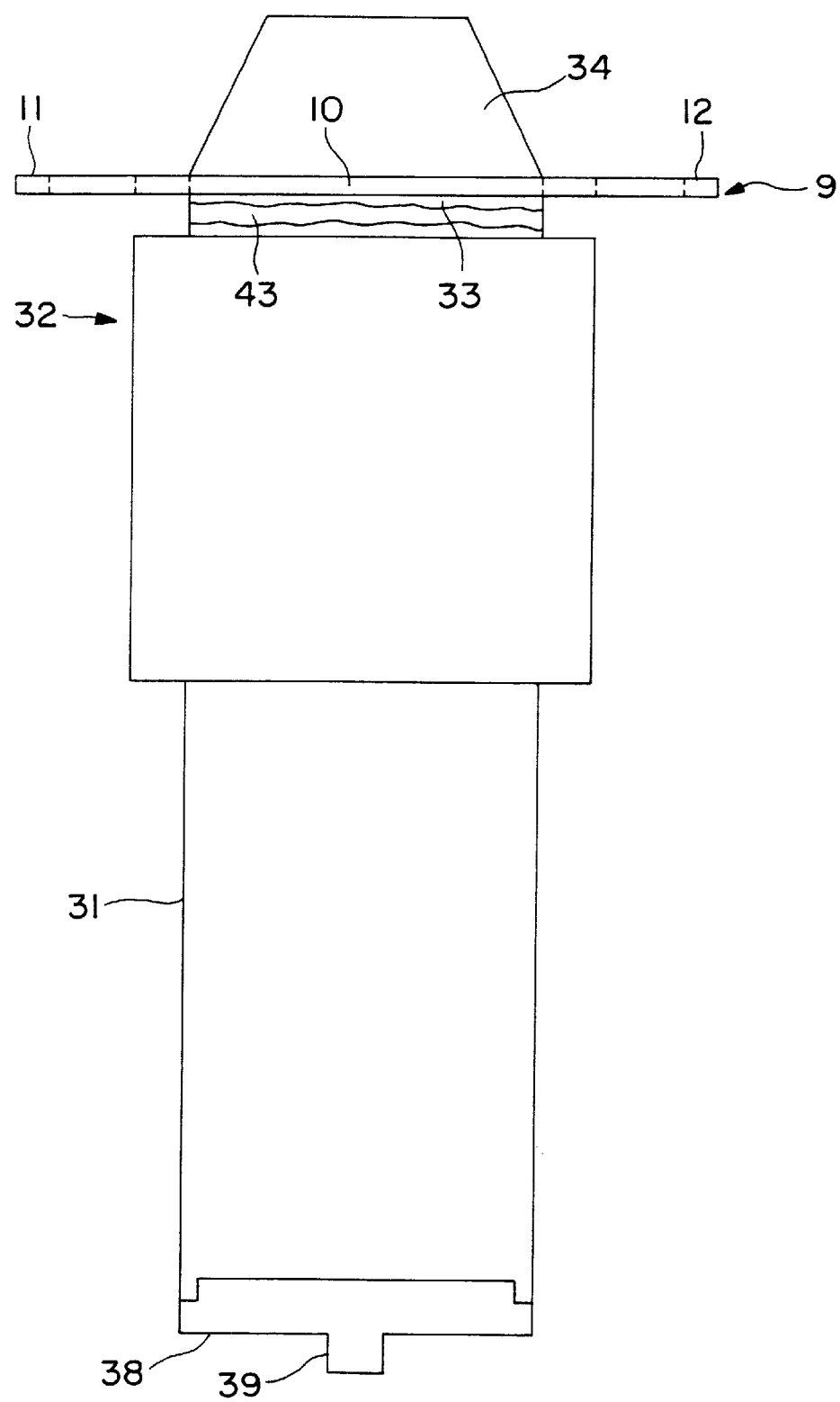
FIG. 15 is a planar view of the vacuum assembly of FIG. 14 showing the tapered penile tube with a constriction ring placed partially upon the transfer sleeve and after removal of the mounting cone.
Figure 16:
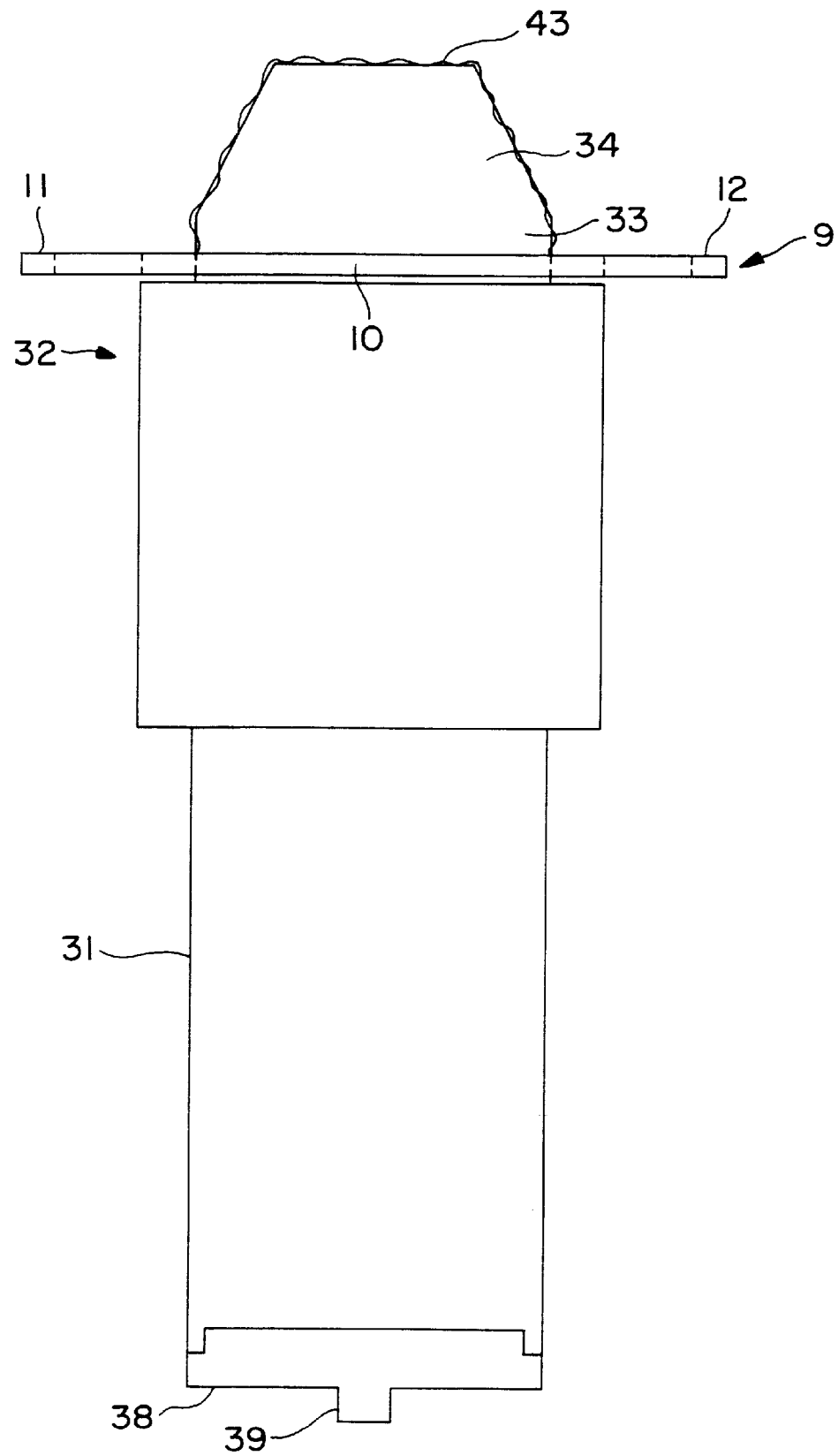
FIG. 16 is a planar view of the vacuum assembly of FIG. 15 showing the constriction ring fully mounted on the transfer sleeve of the tapered penile tube and ready for placement upon a penis.

Assembly and use of the vacuum system of the present invention will be discussed with reference to FIGS. 14–18. FIG. 14 shows a constriction ring 9 in the process of being mounted onto transfer sleeve 33 of penile tube 31. This is accomplished by, first, holding and pulling on loops 11 and 12 of constriction ring 9 to enlarge center ring 10. Next enlarged center ring 10 is slid over conical portion 41 of mounting cone 40 and onto transfer sleeve 33 so that it is slightly spaced from removal guide 32 as shown in FIG. 15. Mounting cone 40 is then removed and lubricant 43 is applied to the transfer sleeve 33 as shown in FIG. 15. Constriction ring 9 is then slid over the lubricated portion of transfer sleeve 33 so that it rests against removal guide 32 as shown in FIG. 16 with the interior portions of center ring 10 and loops 11 and 12 being illustrated by dotted lines. In this position, constriction ring 9 is mounted and ready for insertion upon a penis. As shown in FIG. 16, additional lubricant 43 is applied to the inner and outer surfaces of tapered end 34 and to transfer sleeve 33. Preferably, lubricant 43 is a water soluble lubricating jelly such as K-Y™ lubricating jelly available from Johnson and Johnson Medical, Inc., Arlington, Tex.

Figure 17:
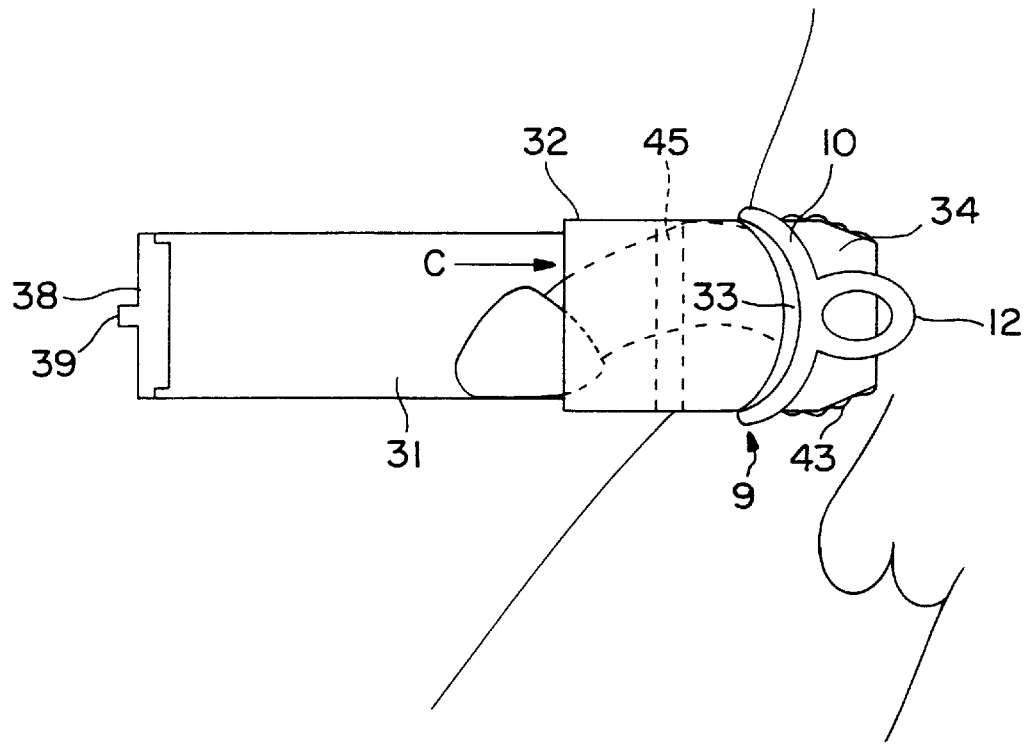
FIG. 17 is a planar view of the vacuum assembly of FIG. 16 showing a tapered penile tube with a constriction ring in the process of being placed upon the base of a penis to be erected.

Shown in FIG. 17 is a user having a flaccid penis inserted into the penile tube 31 with a constriction ring 9 mounted on transfer sleeve 33, as described above with respect to FIG. 16. The penile tube 31 is rotated so that loops 11 and 12 of mounted constriction ring 9 point to the sides of the user's body. The tapered end 34 of penile tube 31 is typically lubricated and slight pressure is applied to the penile tube 31 toward the body of the user in order to assist in sealing penile tube 31 against the user's body so that a vacuum may be drawn. By attaching a vacuum source (not shown) to nozzle 39 of vacuum cap 38, a vacuum is drawn in penile tube 31 which causes the penis to become engorged with blood, thus achieving an erection.

As soon as the desired erection has been achieved, the constriction ring 9 is then placed at the base of the penis to maintain the state of engorgement with blood. As shown in FIG. 17, this is accomplished by pushing removal guide 32 along the longitudinal axis of the penile tube 31 toward the user in the direction of arrow C without the need for any substantial rotational motion. The movement of removal guide 32 in this manner forces constriction ring 9 to slide off of the transfer sleeve 33 and onto tapered end 34 without subjecting penile tube 31 to any rocking or twisting forces. Once the constriction ring 9 has slid onto tapered end 34 of penile tube 31, the elastic force stored by the expanded constriction ring 9 is released which self-propels the constriction ring 9 over tapered end 34 onto the base of the penis. No additional force need be applied to the removal guide 32 once the constriction ring 9 is moved onto tapered end 34 because the decreasing outer diameter provided by tapered end 34 in conjunction with lubricant 43 permits elastic constriction ring 9 to contract and "catapult" onto the base of the penis. Upon placing the constriction ring 9 on the penis, center ring 10 contracts onto the base or root of the erect penis to prevent outflow of venous blood drawn by the vacuum created within the penile tube 31.

Figure 18:
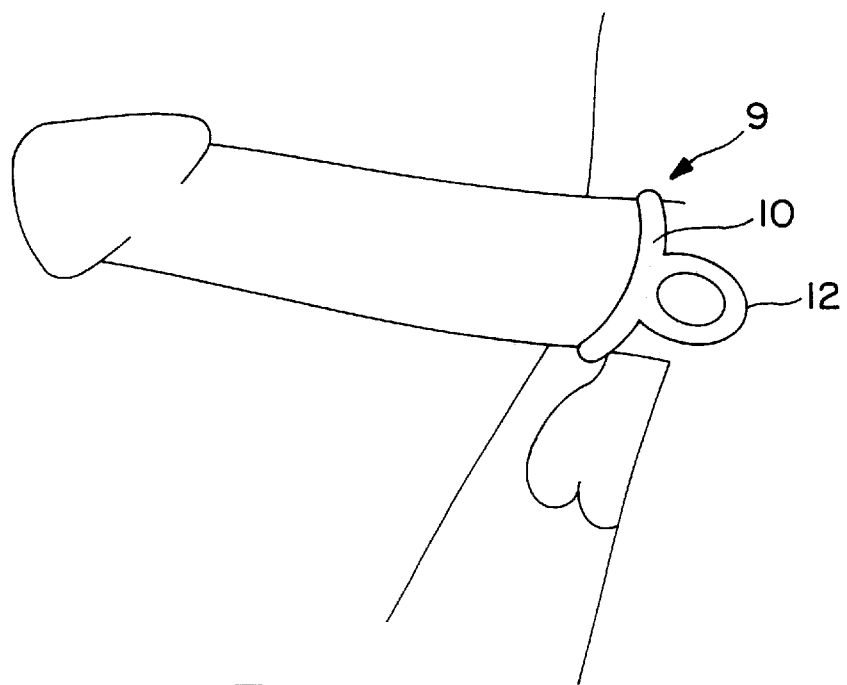
FIG. 18 is a planar view of an erect penis with a constriction ring placed upon the base of the penis and after removal of the vacuum assembly according to the present invention.

The final step to permit the user to engage in sexual intercourse, is the removal the vacuum system from the body of the user. This is accomplished by disconnecting the vacuum source (not shown) from nozzle 39 to permit penile tube 31 to be removed from the body of the user. FIG. 18 shows an erect penis with constriction ring 9 placed upon the base of the penis and after removal of the vacuum assembly according to the present invention. Normal intercourse may now be accomplished. As shown in FIG. 18, loops 11 (hidden from view) and 12 of mounted constriction ring 9 point to the sides of the user's body and can be easily grasped by the user to facilitate removal of the constriction ring 9 after normal intercourse is achieved.

Thus, the present invention provides a penile tube 31 with a tapered end 34 which facilitates movement of a constriction ring over the conical surface provided by tapered end 34 onto a penis. By this arrangement the present invention thereby substantially eliminates the need for the rocking motion required by conventional vacuum systems to transfer the constriction ring thereby preventing loss of vacuum during use and facilitating operation without the need for assistance by persons other than the user of the system. The present invention also provides a removal guide 32 with a stepped inner surface which fits over a stop ring 45 located on the penile tube. As a result of these improvements the present invention facilitates the placement of a configuration ring upon a penis while maintaining a vacuum in the penile tube.

Figure 19:
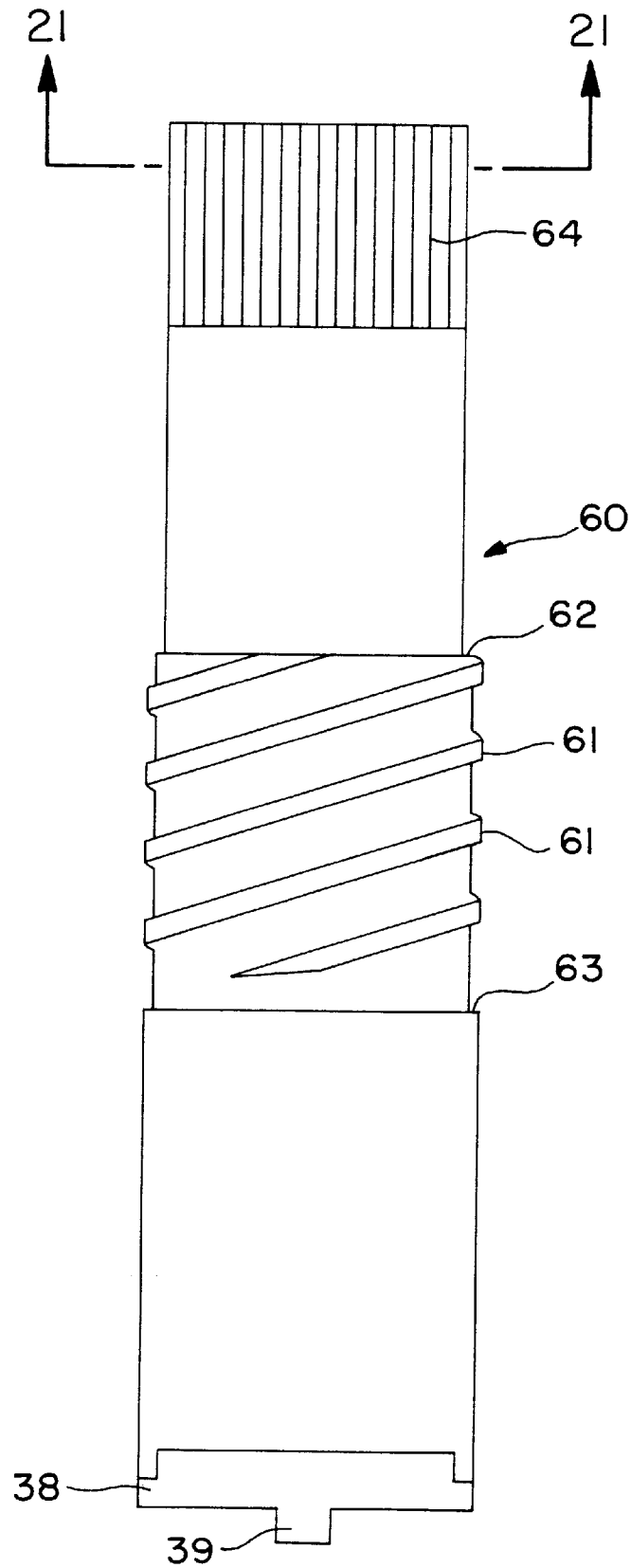
FIG. 19 is a planar view of a threaded penile tube having a ribbed end according to the present invention.
Figure 20:
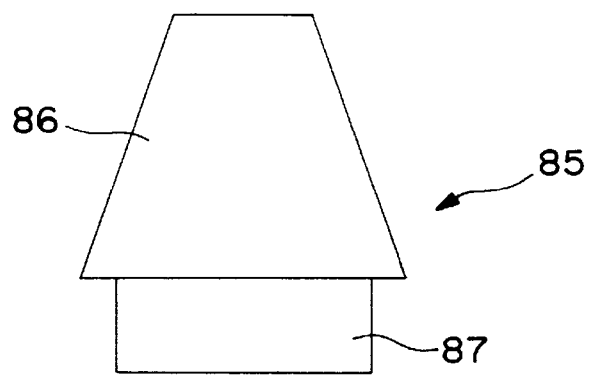
FIG. 20 is a planar view of a mounting cone according to the present invention.
Figure 21:
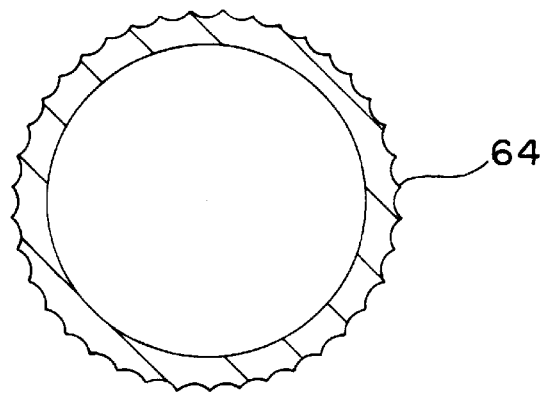
FIG. 21 is a cross-sectional view of the ribbed transfer sleeve of FIG. 19 taken along the sectional line 21—21.

An additional embodiment of the present invention is shown in FIGS. 19–29 which incorporates a threaded penile tube 60 with circumferentially located threads 61 as shown in FIG. 19. Threaded penile tube 60 has a ribbed end having a ribbed transfer sleeve portion 64 with a ribbed or fluted cross-sectional profile as shown in FIG. 21. Outer stepped portions 62 and 63 may be located on the outer surface of threaded penile tube 60 to provide a means for stopping and positioning threaded removal guide 70 during mounting of a constriction ring 9 as discussed below. Threads 61, outer stepped portions 62 and 63, and ribbed transfer sleeve portion 64 are preferably provided during manufacture of threaded penile tube 60 which preferably is by injection molding a transparent plastic. Although molding processes generally are preferred due to cost considerations, inter alia, it will be readily recognized that other manufacturing techniques may also be employed. For example, threads 61, outer stepped portions 62 and 63, and ribbed transfer sleeve portion 64 may be machined into the surface of an extruded plastic tube to form threaded penile tube 60.

Figure 26:
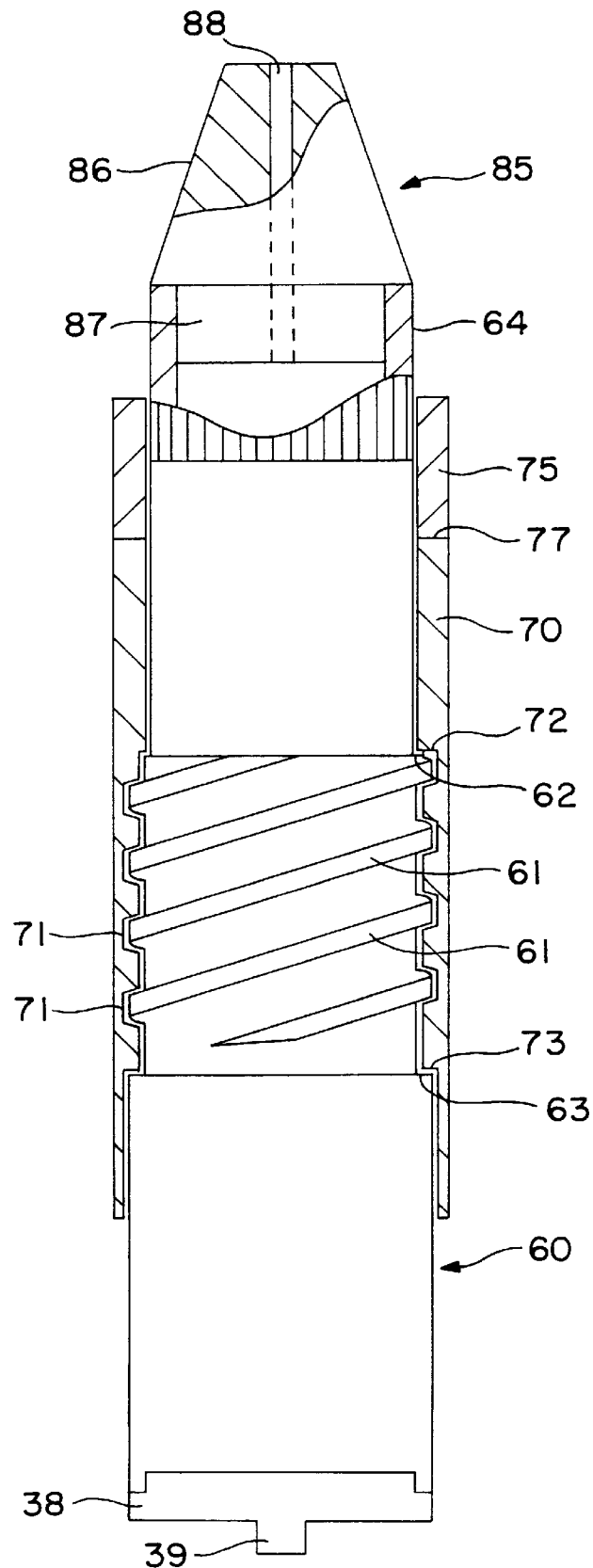
FIG. 26 is a partial cross-sectional view of the threaded penile tube of FIG. 19 with a threaded removal guide and spacer sleeve located concentrically on the threaded penile tube and a mounting cone assembled to the ribbed end of the threaded penile tube according to the present invention.

FIG. 20 shows a mounting cone 85 which has frustroconical portion 86 to facilitate sliding a constriction ring 9 onto the ribbed transfer sleeve 64 of threaded penile tube 60. Mounting cone 85 has a cylindrical end 87 which fits into the interior of ribbed transfer sleeve 64 as shown in FIG. 26. A cylindrical hole is located along the longitudinal axis of mounting cone 85 to provide an air vent 88 which facilitates insertion and removal of mounting cone 85 by permitting air to pass out of and into threaded penile tube 60, respectively.

Figure 22:
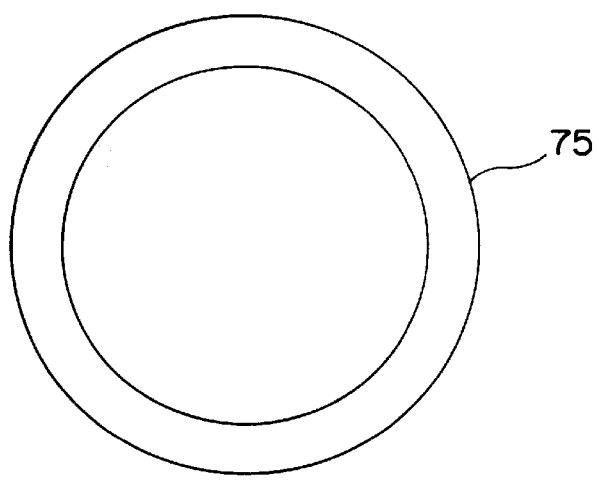
FIG. 22 is a front planar view of a spacer sleeve according to the present invention.
Figure 23:
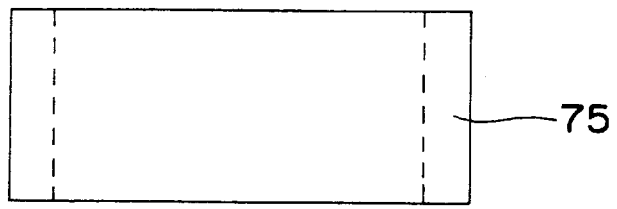
FIG. 23 is a side planar view of a spacer sleeve according to the present invention.
Figure 24:
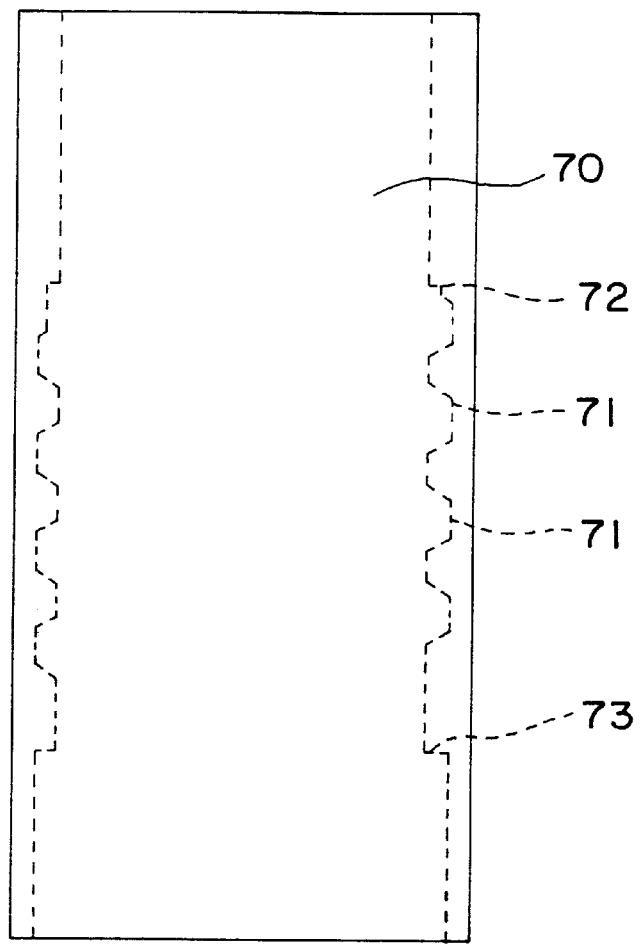
FIG. 24 is a side planar view of a threaded removal guide according to the present invention.

FIGS. 22 and 23 show a spacer sleeve 75 and FIG. 24 shows a threaded removal guide 70 having inner surfaces illustrated by dashed lines which are configured to engage the outer surface of threaded penile tube 60 as shown in FIG. 26. Threaded removal guide 70 has threads 71 which are configured to engage threads 61 of threaded penile tube 60. Threaded removal guide 70 may also be provided with inner flanges 72 and 73, either individually or in combination, to respectively engage outer stepped portions 62 and 63 of threaded penile tube 60. Spacer sleeve 75 and threaded removal guide 70 are preferably made of a molded plastic produced by injection molding or other molding process.

The surfaces of spacer sleeve 75 and threaded removal guide 70 which meet when these components are placed next to each other may be machined, manufactured from or coated with materials having a low coefficient of friction, or both, in order to reduce the friction at joint 77 shown in FIGS. 25–29.

Figure 25:
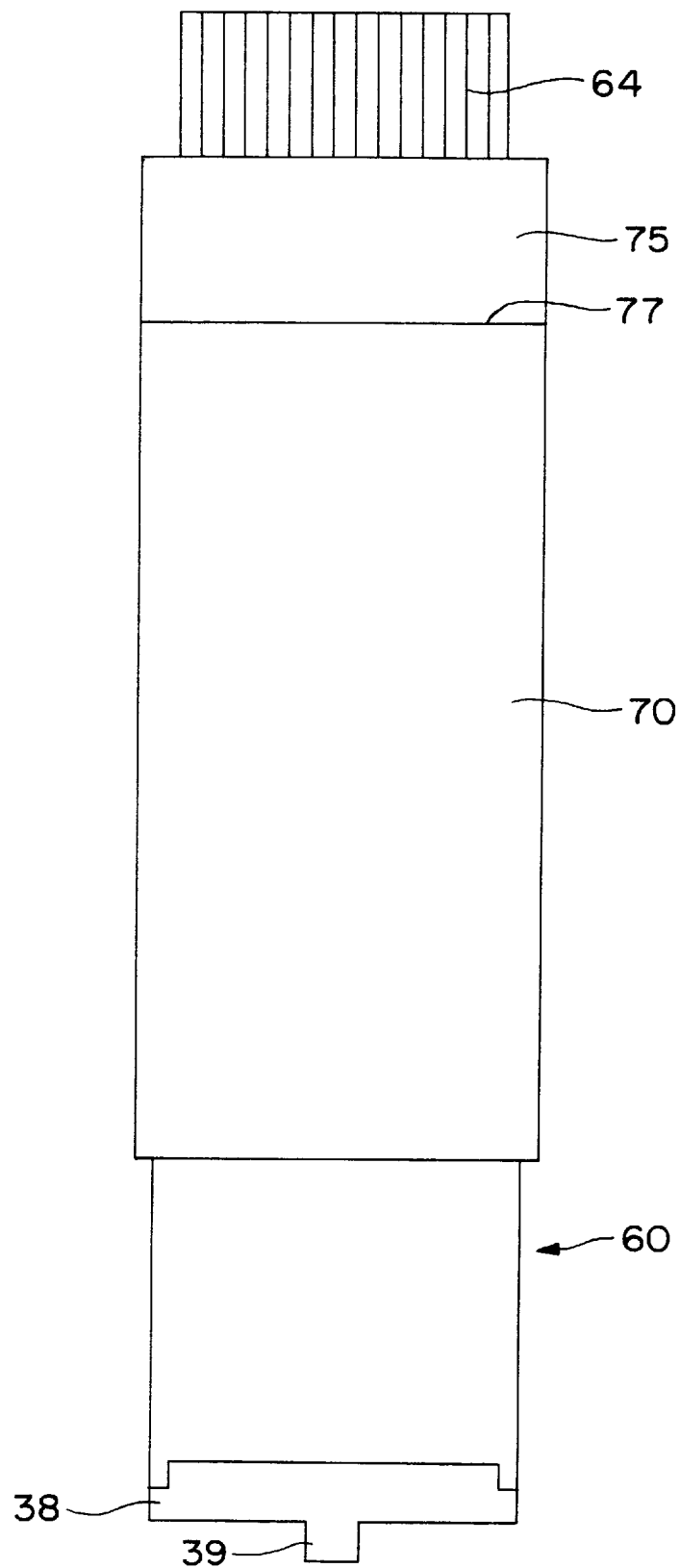
FIG. 25 is a planar side view of the threaded penile tube of FIG. 19 with a threaded removal guide and spacer sleeve located concentrically on the threaded penile tube according to the present invention.

Assembly of the vacuum system of a second embodiment of the present invention will be discussed with reference to FIGS. 25–29. As shown in FIG. 25, threaded removal guide 70 and spacer sleeve 75 are located concentrically on the threaded penile tube 60. This is accomplished by inserting and rotating threaded penile tube 60 in the interior of threaded removal guide 70 so that threads 61 engage threads 71. Spacer sleeve 75 is centered over threaded penile tube 60 and placed against threaded removal guide 70. Depending on the thread configuration of threads 61 and 71, threaded removal guide 70 is then rotated either clockwise or counterclockwise to helically move threaded removal guide 70 along the longitudinal axis of threaded penile tube 60 toward vacuum cap 38 until a desired length of ribbed transfer sleeve 64 is left exposed as shown in FIG. 25. Inner flanges 72 and 73, if provided, may be used to respectively engage outer stepped portions 62 and 63 to stop threaded removal guide 70 from further rotation once the desired length of ribbed transfer sleeve 64 is exposed. The length of ribbed transfer sleeve 64 which can be exposed is predetermined and may be changed by varying the position of the stop means provided by outer stepped portions 62 and 63, inner flanges 72 and 73, or both, to define the range of motion of threaded removal guide 70 along threaded penile tube 60. Preferably, approximately a one inch portion of ribbed transfer sleeve 64 is left exposed to provide ample room to accommodate for stretching of and facilitate mounting of constriction ring 9 thereon.

Figure 27:
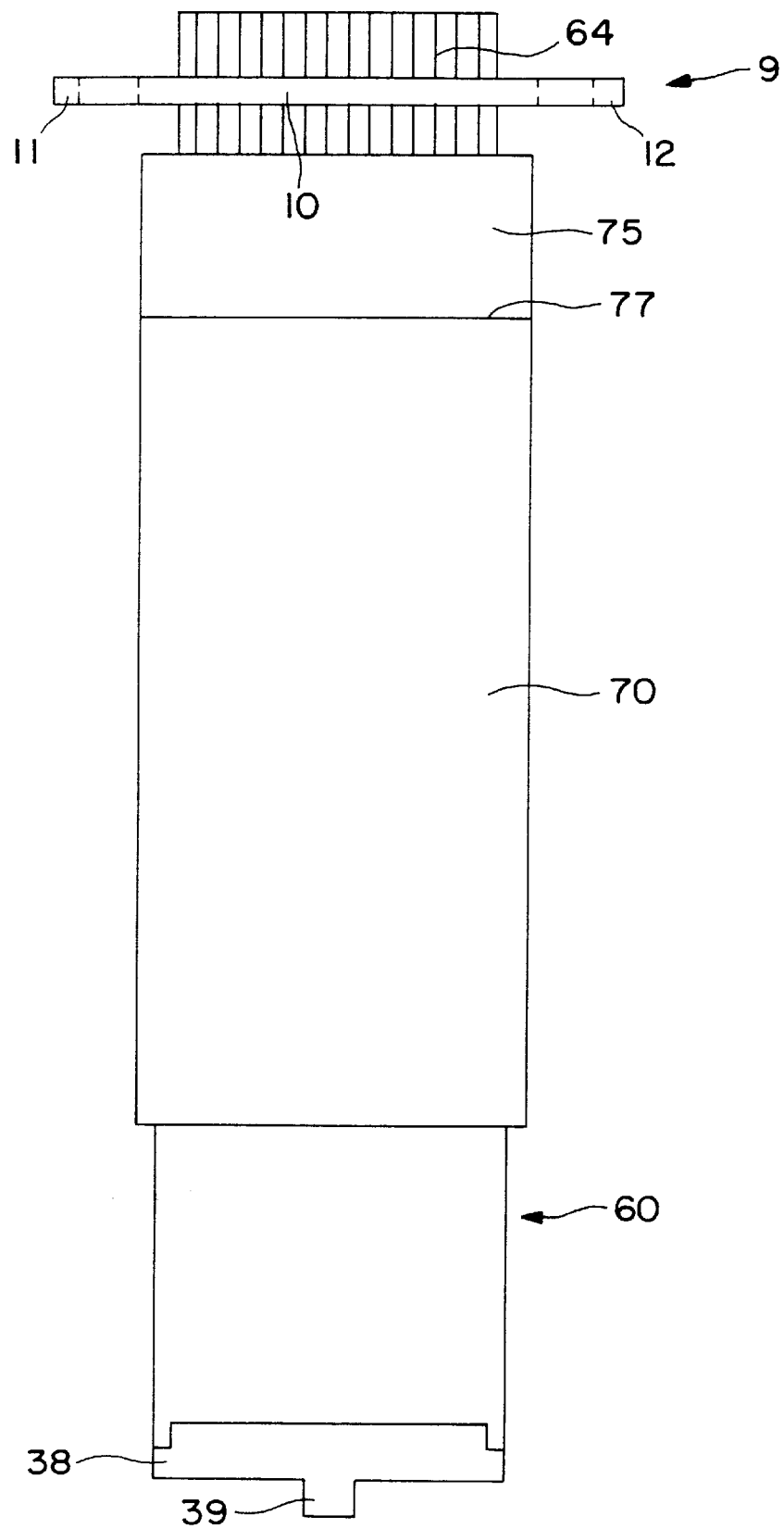
FIG. 27 is a planar side view of the threaded penile tube, threaded removal guide, and spacer sleeve of FIG. 26 with a constriction ring placed upon the ribbed transfer sleeve and after removal of the mounting cone.

As shown in FIG. 26, mounting cone 85 is assembled to the ribbed end of the threaded penile tube 60 by inserting cylindrical end 87 into ribbed transfer sleeve 64. Constriction ring 9 is then mounted onto ribbed transfer sleeve 64 of threaded penile tube 60 in similar fashion as discussed above with respect to the first embodiment by first, holding and pulling on loops 11 and 12 of constriction ring 9 to enlarge center ring 10. Next enlarged center ring 10 is slid over frustro-conical portion 86 of mounting cone 85 onto ribbed transfer sleeve 64 so that it is slightly spaced from spacer sleeve 75 and mounting cone 85 is then removed as shown in FIG. 27. The interior portions of center ring 10 and loops 11 and 12 of constriction ring 9 are shown illustrated by dotted lines.

Figure 28:
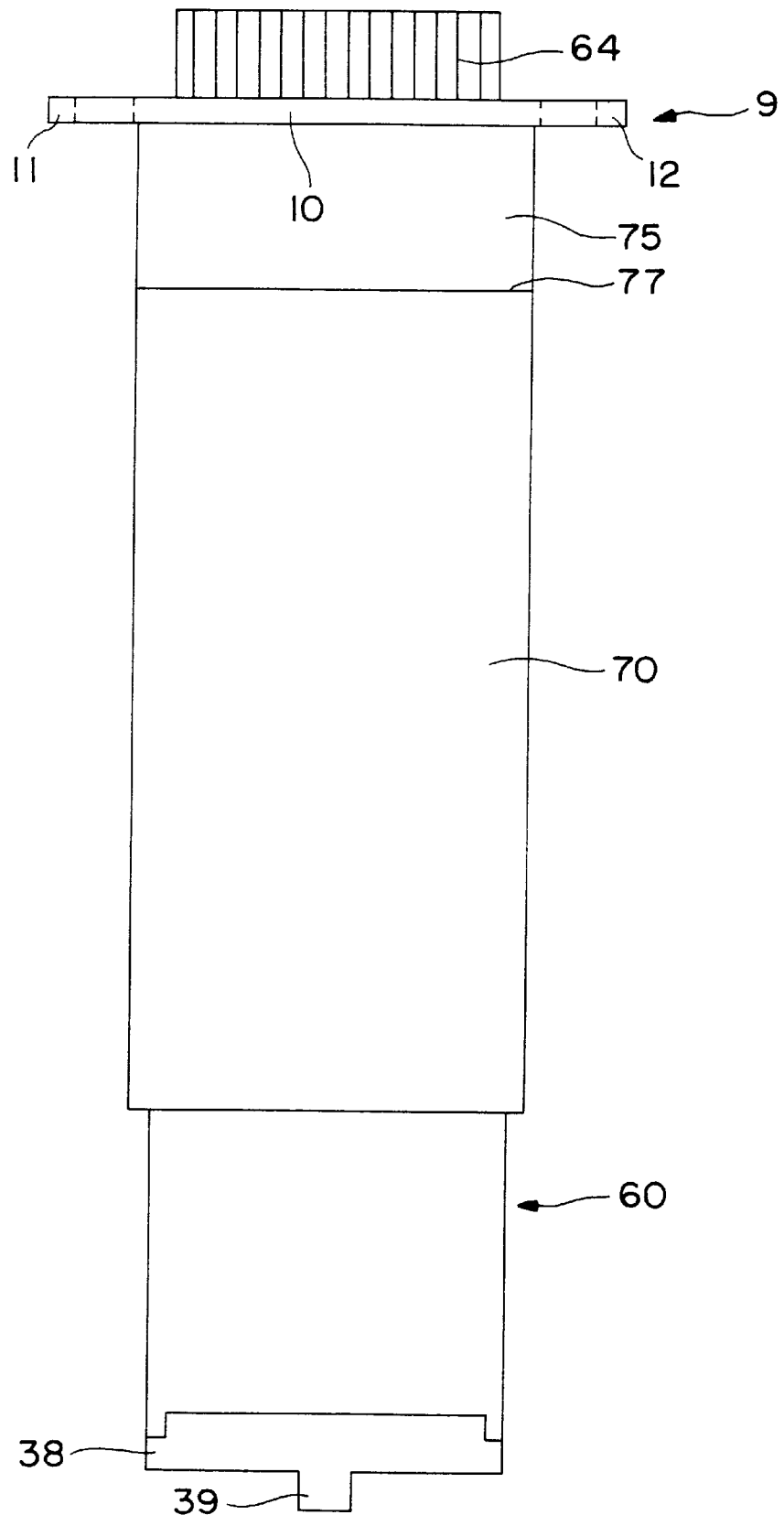
FIG. 28 is a planar side view of the threaded penile tube, threaded removal guide, and spacer sleeve of FIG. 27 after moving spacer sleeve forward to contact the constriction ring.
Figure 29:
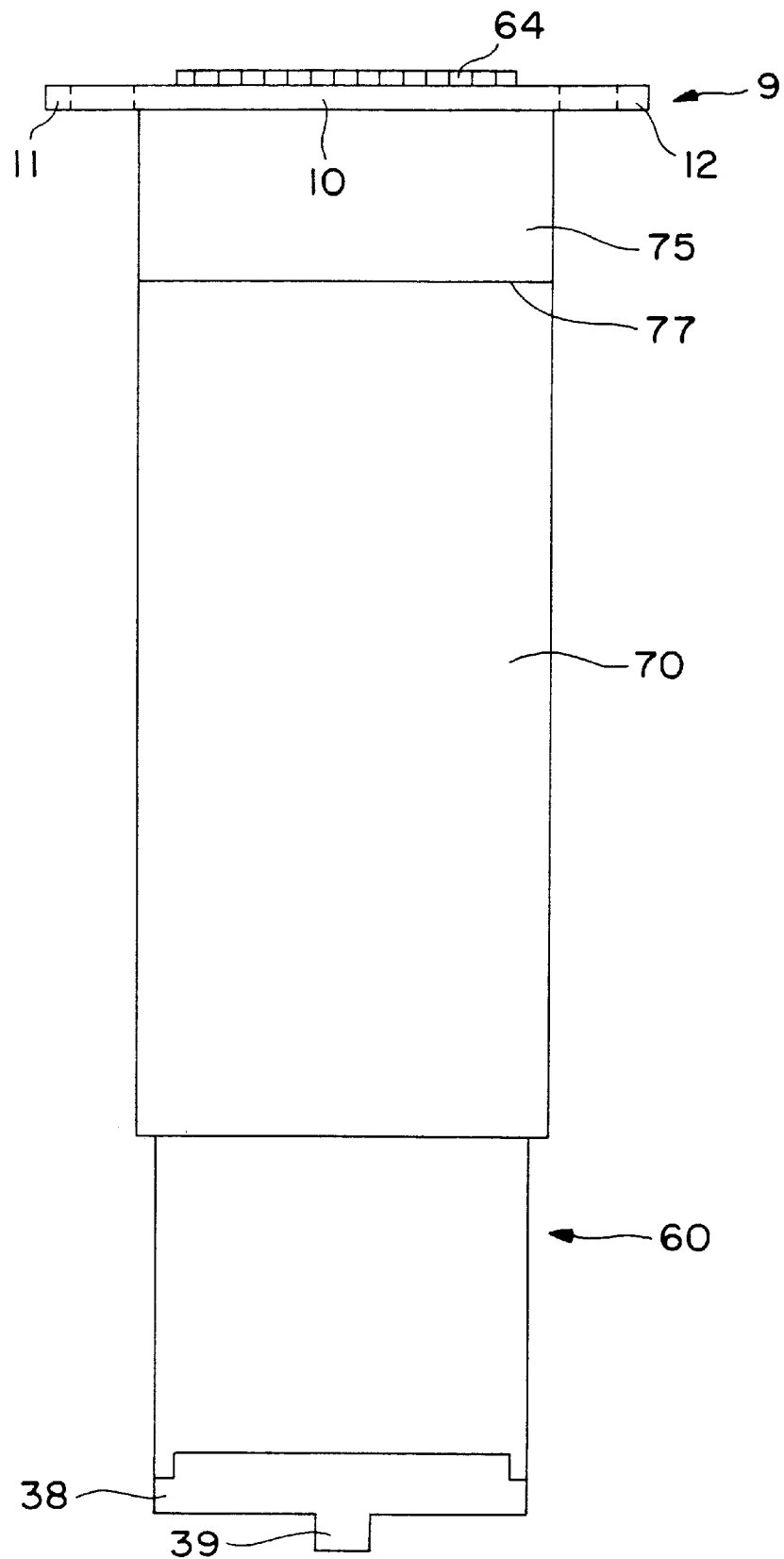
FIG. 29 is a planar side view of the threaded penile tube, threaded removal guide, and spacer sleeve of FIG. 28 showing the constriction ring moved near the edge of the ribbed transfer sleeve of the threaded penile tube and ready for placement upon a penis.

Threaded removal guide 70 is rotated to push and advance spacer sleeve 75 to rest against constriction ring 9 as shown in FIG. 28. Threaded removal guide 70 is rotated further to push and advance spacer sleeve 75 which, in turn, pushes constriction ring 9 causing it to slide over ribbed transfer sleeve 64. Rotation of threaded removal guide 70 is continued until constriction ring 9 rests near the end of the ribbed transfer sleeve 64 as shown in FIG. 29. In this position, constriction ring 9 is mounted and ready for insertion upon a penis which is accomplished by further rotating threaded removal guide 70 after a penis has been placed inside threaded penile tube 60 and made erect by the application of a vacuum to nozzle 39 of vacuum cap 38. In this manner, by moving constriction ring 9 to rest close to the end of ribbed transfer sleeve 64 prior to the insertion of a penis into threaded penile tube 60, the distance which constriction ring 9 must be moved onto an erect penis may be minimized. As a result, the process of mounting the constriction ring 9 onto the penis of a user is expedited and facilitated because only a minimal amount of additional rotation of threaded removal guide 70 is required to move constriction ring 9 across a short distance off of the ribbed transfer sleeve 64.

Use of the assembled vacuum system is substantially similar to that as described for the first embodiment, which disclosure is incorporated herein, with two modifications. The first modification is that ribbed transfer sleeve 64 according to the second embodiment provides a surface having lower friction to facilitate the sliding of center ring 10 of constriction ring 9 onto and off of the ribbed transfer sleeve 64. As a result, mounting of constriction ring 9 onto and subsequent removal of constriction ring 9 off of threaded penile tube 60 may be accomplished without the need for lubricant on the surface of ribbed transfer sleeve 64. The second modification is provided by the incorporation of a threaded penile tube 60 and threaded removal guide 70 assembly in conjunction with spacer sleeve 75 which facilitates the removal of constriction ring 9 from ribbed transfer sleeve 64 upon rotating threaded removal guide 70 to helically it move toward ribbed transfer sleeve 64. The forward rotational motion of threaded removal guide 70 causes an axial force which pushes spacer sleeve 75 to move along the longitudinal axis of the threaded penile tube 60 toward the end of ribbed transfer sleeve 64. The movement of spacer sleeve 75 in this manner forces constriction ring 9 to slide off of ribbed transfer sleeve 64 a short distance onto the penis of a user without the need for great strength or dexterity on the part of the user. By providing spacer sleeve 75 between threaded removal guide 70 and constriction ring 9, the translation of the forward rotational (i.e., helical) movement of threaded removal guide 70 into a forward axial motion (which ultimately moves constriction ring 9 via spacer sleeve 75) is facilitated by eliminating the friction created by rotating ribbed transfer sleeve 64 directly against constriction ring 9, which typically is made of a silicone rubber. Rotation of threaded removal guide 70 may be further facilitated by providing riding surfaces between threaded removal guide 70 and spacer sleeve 75 which reduce the friction at joint 77 as discussed above.

Thus, the present invention also provides a vacuum assembly having substantially reduced frictional forces between the components of the vacuum assembly thereby eliminating the need for great strength or dexterity on the part of the user and facilitating operation without the need for assistance by persons other than the user of the system. The reduction in frictional forces is accomplished by first providing a threaded penile tube 60 with a ribbed transfer sleeve 64 having a ribbed or fluted surface which facilitates movement of a constriction ring over the ribbed transfer sleeve 64 onto a penis. Additionally, a threaded penile tube 60 and threaded removal guide 70 assembly in conjunction with a spacer sleeve 75 facilitates the removal of constriction ring 9 from ribbed transfer sleeve 64 by eliminating the friction created by rotating ribbed transfer sleeve 64 directly against constriction ring 9. An alternative mounting cone 85 is also provided which fits into the interior of ribbed transfer sleeve 64 and has a cylindrical hole located along the longitudinal axis to facilitate insertion and removal of mounting cone 85.

As a result of these improvements the present invention facilitates the placement of a configuration ring upon a penis while maintaining a vacuum in the penile tube.

It is envisioned and to be understood that the various configurations of the various conventional components shown in the figures used in the apparatus for conditioning a male organ of the present invention may be incorporated either in place of or in combination with any of the configurations disclosed to the extent that the parts are interchangeable. For example, it will be readily recognized that a vacuum pump 20 may be used in place of a vacuum source and vacuum cap 38 by inserting a vacuum pump 20, shown in FIG. 4, directly into the penile tube 31 at the end opposite tapered end 34. Although illustrated and described with reference to certain specific embodiments, the present invention is nevertheless not intended to be limited to the details shown. Rather, it is envisioned that various components of the embodiments shown may be used interchangeably, where functionally possible, and that various modifications may be made in the details within the scope and range of equivalents of the claims and without departing from the spirit of the invention.

What is claimed:

1. A penile tube and constrictor ring removal guide system for use in a vacuum therapy system for achieving and maintaining an erection, the penile tube and removal guide system comprising:
 a penile tube having:
  i) a first open, tapered end adapted to accept a penis, and
  ii) a second end adapted to accept a vacuum source;
 removal guide disposed concentrically about the penile tube and having a stepped inner surface defining:
  i) a larger inner diameter portion toward the second end, and
  ii) a smaller inner diameter portion toward the first end; and
 a stop ring disposed between the first end and the second end provided to limit movement of the removal guide along the penile tube.

2. The penile tube and removal guide system according to claim 1 wherein the stop ring is moveable along the longitudinal axis of the penile tube.

3. The penile tube and removal guide system according to claim 2 wherein the stop ring is positioned along the penile tube toward the first end, the stepped inner surface of the removal guide engaging the stop ring as the removal guide moves toward the first end of the penile tube.

4. The penile tube and removal guide system according to claim 1 further comprising a mounting cone having:
 i) a conical portion, and
 ii) a cylindrical end having an inner surface defining a recess adapted to fit over the first end of the penile tube.

5. The penile tube and removal guide system according to claim 1 further comprising a vacuum cap inserted into the second end of the penile tube having a nozzle adapted for attachment of a vacuum source.

6. A penile tube and constrictor rind removal guide system for use in a vacuum therapy system for achieving and maintaining an erection comprising:
 a threaded penile tube having:
  i) a first ribbed transfer end having a ribbed surface, and
  ii) a second end adapted to accept a vacuum source; and
 a threaded removal guide assembly concentrically engaging the threaded penile tube.

7. The penile tube and removal guide system according to claim 6 further comprising a mounting cone adapted to be inserted into and removed from the interior of ribbed transfer sleeve.

8. The penile tube and removal guide system according to claim 7 wherein the mounting cone has a portion forming a cylindrical hole facilitating insertion and removal of the mounting cone.

9. The penile tube and removal guide system according to claim 6 further comprising a vacuum cap inserted into the second end of the penile tube having a nozzle adapted for attachment of a vacuum source.

10. The penile tube and removal guide system according to claim 6 further comprising a spacer sleeve removably placed concentrically on the penile tube between the threaded removal guide and the first end of the penile tube.

11. The penile tube and removal guide system according to claim 6 wherein:
 the threaded removal guide has a stepped inner surface defining:
  i) a larger inner diameter portion toward the second end, and
  ii) a smaller inner diameter portion toward the first end; and
 the penile tube has at least one stepped outer surface defining:
  i) a larger outer diameter portion toward the second end, and
  ii) a smaller outer diameter portion toward the first end.

12. A method for assisting the development of a penile erection, the method comprising the steps of:
 placing a stop ring onto a penile tube,
 placing a removal guide onto the penile tube,
 placing a mounting cone over a first tapered end of the penile tube,
 stretching and placing a constriction ring over the mounting cone and onto the penile tube beyond the tapered section of the penile tube,
 removing the mounting cone,
 placing a penis into the penile tube,
 drawing a vacuum from a second end of the penile tube,
 after achieving an erect penis, sliding the removal guide toward the first end until the constriction ring slides off of the first tapered end of the penile tube onto the base of the erect penis,
 removing the vacuum source, and
 removing the penile tube.

13. The method of claim 12 wherein a lubricant is used to aid in the movement of the constriction ring and the removal guide.

14. A method for assisting the development of a penile erection, the method comprising the steps of:
 placing a threaded removal guide onto a threaded penile tube,
 placing a mounting cone over a first ribbed end of the penile tube,
 stretching and placing a constriction ring over the mounting cone and onto the ribbed end of the penile tube,
 removing the mounting cone,
 placing a penis into the penile tube,
 drawing a vacuum from a second end of the penile tube,
 after achieving an erect penis, screwing the removal guide toward the first end until the constriction ring slides off of the ribbed end of the penile tube onto the base of the erect penis,
 removing the vacuum source, and
 removing the penile tube.

15. The method of claim 14 wherein a lubricant is used to aid in the movement of the constriction ring off of the ribbed end of the penile tube.

* * * * *